(12) United States Patent
Cervi (10) Patent No.: US 7,722,548 B2
(45) Date of Patent: May 25, 2010

(54) BIOPSY DEVICE

(76) Inventor: Paul Laurence Cervi, 23 Holmwood Avenue, Shenfield, Essex CM15 8QS (GB)

( * ) Notice: Subject to any disclaimer, the term of this patent is extended or adjusted under 35 U.S.C. 154(b) by 856 days.

(21) Appl. No.: 10/258,323

(22) PCT Filed: Apr. 12, 2001

(86) PCT No.: PCT/GB01/01674

§ 371 (c)(1),
(2), (4) Date: Apr. 25, 2003

(87) PCT Pub. No.: WO01/80743

PCT Pub. Date: Nov. 1, 2001

(65) Prior Publication Data

US 2003/0171766 A1    Sep. 11, 2003

(30) Foreign Application Priority Data

Apr. 20, 2000    (GB) .................................. 0009927.5

(51) Int. Cl.
*A61B 10/00* (2006.01)
*A61B 17/32* (2006.01)
*A61B 17/14* (2006.01)
*A61B 17/34* (2006.01)

(52) U.S. Cl. ........................ 600/564; 600/562; 600/568; 606/171; 606/177; 606/183; 606/185; 606/187

(58) Field of Classification Search ................. 600/562, 600/564, 568; 606/183, 171, 177, 185, 187
See application file for complete search history.

(56) References Cited

U.S. PATENT DOCUMENTS 3,683,892 A * 8/1972 Harris ........................ 600/567
3,998,229 A * 12/1976 Barton ........................ 606/167
4,651,752 A * 3/1987 Fuerst ........................ 600/567

(Continued)

FOREIGN PATENT DOCUMENTS

FR        2 493 137        11/1980

(Continued)

OTHER PUBLICATIONS

English abstract of FR 2 493 137.

*Primary Examiner*—Max Hindenburg
*Assistant Examiner*—Jeffrey G Hoekstra
(74) *Attorney, Agent, or Firm*—Fish & Richardson P.C.

(57) ABSTRACT

A soft tissue biopsy device is provided which allows for the recovery of a biopsy of tissue flat in shape, particularly suitable for lymph node biopsy. The device includes twin opposing primary blades preferably aligned in parallel planes, to cut the upper and lower surfaces of the biopsy. A detachment blade is provided to cut the side walls and distal ends of the biopsy. In a preferred embodiment, each primary blade has a sharpened tip set at an angle with a sharpened point to assist tissue penetration. The detachment blade, preferably has inwardly curving flexible sharpened tips at its distal end, and is attached to the handle at its proximal end by a slider such that when in a retracted position, the detachment blade is retracted from the tip of the twixt blades; and when in an advanced position, the tip of the detachment blade abuts the tip of the twin blades.

30 Claims, 7 Drawing Sheets

U.S. PATENT DOCUMENTS

| | | | |
|---|---|---|---|
| 5,471,992 A * | 12/1995 | Banik et al. | 600/564 |
| 5,570,700 A * | 11/1996 | Vogeler | 600/567 |
| 5,846,244 A * | 12/1998 | Cripe | 606/82 |
| 5,885,226 A * | 3/1999 | Rubinstein et al. | 600/564 |
| 5,922,000 A * | 7/1999 | Chodorow | 600/567 |
| 6,264,668 B1 * | 7/2001 | Prywes | 606/167 |
| 6,497,651 B1 * | 12/2002 | Kan et al. | 600/114 |
| 6,517,498 B1 * | 2/2003 | Burbank et al. | 600/564 |

FOREIGN PATENT DOCUMENTS

| | | |
|---|---|---|
| FR | 2 791 433 | 9/2000 |
| WO | WO 93/19675 | 10/1993 |

* cited by examiner

BIOPSY DEVICE

This invention is generally concerned with apparatus and methods for obtaining biopsy samples from human and animal tissue. More particularly it relates to improvements in sampling soft tissue, such as lymph node tissue.

Soft tissue biopsy sampling is a common and important investigation in medical and surgical practice. Biopsy samples are generally obtained using a biopsy device based around a hollow round needle or cannula design resulting in the retrieval of cylindrical section of tissue. While this has the advantage of allowing deep penetration into tissues, the result is frequently a narrow or small specimen which may make accurate diagnosis difficult. Furthermore, there is no intrinsic reason why the biopsy sample should be cylindrical in shape, as the histopathologist will process the sample by cutting it into very thin sections or slices, typically 0.004 mm in thickness, before applying them to glass slides for subsequent staining and microscopic examination. The cylindrical specimen is therefore wasteful as only a very small proportion of the tissue will be examined. In addition, the wound created by a cylindrical device is more liable to bleed because the sides of the wound which remain do not easily oppose one another.

Similar problems arise in the specialized field of lymph node biopsy. Lymph nodes are commonly enlarged in superficial sites, because of infection, or infiltration by tumour and lymph node examination is frequently necessary for diagnosis. Sometimes, needle aspiration of the lymph node will result in the withdrawal of cells which can be examined cytologically—but this technique, while generally useful in distinguishing benign and malignant conditions, does not usually determine a full diagnosis especially where malignancy is suspected. It is possible to obtain a diagnosis of an enlarged lymph node in a proportion of patients with a conventional cylindrical biopsy needle, but the narrow specimens which result, make it difficult for the histopathologist to make a fill diagnosis. In particular, patchy abnormalities may be missed, and the architecture of the lymph node may not be easily ascertained. Many histopathologists recommend open lymph node excision, so that a complete lymph node (measuring between one and five cms diameter) is excised. This frequently means subjecting the patient to a larger than necessary surgical procedure (as only a very thin slide of the node will be generally examined) and frequently results in an operation being undertaken using a general anaesthetic, rather than local anaesthetic. The need for a general anaesthetic is preferably to be avoided as it greatly increases the inconvenience to the patient and to the doctor, increases the risk to the patient, causes a delay in making a diagnosis, and increases the expense of the procedure.

A biopsy device which attempts to address some of these problems is known from U.S. Pat. No. 3,800,783 Jamshidi. This describes a muscle biopsy device comprising a generally rectangular blade with a tapered, cutting distal tip and a backwardly directed slot in the blade forming a hook with an overhanging, sample-retaining barb. A sheath can be slid over the blade after a sample has been captured in the slot, to protect the sample during withdrawal of the biopsy device. This device exhibits some problems in practice, however, in that the tip of the hook must be inserted beyond the tissue to be sampled in order that the barb can engage the sample tissue at the correct point and in that the hook-style design means that the biopsy sample retrieved is relatively small.

Another attempt to address this problem is described in U.S. Pat. No. 4,926,877 Bookwalter, which discloses a broadly conventional device but with the cannula flattened at the sides, and with an extendible, flexible blade to cut the end of the biopsy sample from the surrounding tissue. This device still, however, suffers from the defects associated with conventional designs outlined above.

A parallel-bladed biopsy instrument for obtaining skin samples is described in FR 2,493,137. However in this device the blades penetrate 1-3 mm and are set at at most 5 µm apart, the blades being bent towards one another to sever the tissue sample. Thus the utility of the device is severely limited.

Other biopsy devices of various types are described in U.S. Pat. No. 4,971,067, U.S. Pat. No. 4,168,698, EP 0 919 192A, EP 0 235 489A, U.S. Pat. No. 4,832,045, WO93/19675 and GB 1,084,640.

Accordingly, there exists a need for an improved biopsy device capable of obtaining samples of a larger size than at present, and further capable of providing biopsy samples with flatter, and hence more efficient sections than are available from known devices.

According to the present invention, there is therefore provided a biopsy device comprising a tissue sampler, the tissue sampler comprising a pair of oppositely disposed blades substantially parallel to one another, and substantially planar, the blades defining two sides of a space to receive tissue to be sampled and, at the tip of the device, having front edges to cut the sampled tissue as the device is inserted into the tissue, the tissue sampler further comprising cutting means to cut the sample from the tissue after the device has been inserted.

According to a second aspect of the invention, there is provided a biopsy device comprising twin substantially parallel blades which, when advanced through tissue, cut a thin flat section of tissue biopsy between them, the device further comprising a detachment blade configured to be advanced slidably along the parallel blades to cut away at least a distal end of the biopsy sample.

Another aspect of the invention provides a tissue sampler, the tissue sampler comprising a pair of oppositely disposed blades substantially parallel to one another and substantially planar, the blades defining two sides of a space to receive tissue to be sampled and, at the tip of the device, having front edges to cut the sampled tissue as the device is inserted into the tissue, the pair of blades comprising first and second blades, movable with respect to one another.

In a further aspect the invention provides a biopsy device comprising twin substantially parallel blades which, when advanced through tissue planes, cut a thin flat section of tissue biopsy between them, the device being configured for separate advancement of the twin blades.

The invention further provides a method of obtaining a biopsy sample comprising i) inserting a biopsy device into tissue to be sampled to cut top and bottom edges of the sample; and ii) using the biopsy device to cut side edges of the sample.

The invention further provides a combination of a biopsy device according to the present invention and instructions on a carrier medium, the instructions describing a method of obtaining a biopsy sample, the method comprising: inserting the biopsy device into tissue to be sampled to cut top and bottom edges of the sample; and using the biopsy device to cut at least one side edge of the sample.

By using a pair of oppositely disposed blades whose edges cut the sample tissue as the biopsy device is inserted, it is possible to provide an biopsy device that will sever a relatively large and flat tissue sample from the surrounding tissue. The device can therefore provide a section of tissue of sufficient size for full and efficient histological examination whilst at the same time minimizing trauma to the patient and reducing the risk of bleeding following the procedure. The blades of the tissue sampler are preferably separate or distinct from one another. The two blades can be arranged to define a large tissue receiving space and to give little disturbance to the surrounding tissue, allowing a sample with optimum proportions readily to be obtained. The invention also permits the construction of a biopsy device which is simple and inexpensive to manufacture and straightforward to operate.

The device is based on the recognition that two sharpened blades, when inserted into soft tissue, can cut a slice or section of tissue sample between them without significantly damaging the sample. The device may be used to gather soft tissue such as skin, liver, kidney or tumour tissue from living or dead persons or animals for pathological study. The apparatus is particularly suited to obtaining samples from superficial sites, such as from enlarged lymph nodes, without requiring the patient to undergo extensive or unusual surgical procedures, and without requiring large openings to be formed within the body.

The collection of a relatively large and flat biopsy sample has a number of advantages over the conventional, broadly cylindrical tissue samples. A greater proportion of the sample can be analysed as the shape better conforms to that desired by the histopathologist who is charged with examination of the specimen; there is a greater opportunity of detecting architectural or patchy abnormalities, as a greater contiguous surface area is examined, assisting in obtaining correct diagnosis; and there is less risk of bleeding as the two surfaces of the wound created by the blades of the tissue sampler can be readily opposed by applying external pressure. Particular advantages may be obtained where there is a need to procure large samples for examination, especially where the tissue of interest is superficial or otherwise easily accessible (such as during open surgery or post mortem examination).

A typical biopsy device for soft tissues has a cannula with an internal diameter of approximately 1 mm; larger diameter devices may provide samples up to 2.5 mm diameter. Sample lengths are typically 1 to 2 cm. By comparison, embodiments of the present invention readily allow the provision of samples with a width of between 3 and 15 mm, a thickness of 1 to 2 mm and a length of 1 to 3 cm. In a preferred embodiment samples of approximately 4 mm width by 1 mm thickness are provided, though these values can be readily adjusted to suit the requirements of a particular application. Smaller samples, for example of less than 1 cm in length and/or less than 1 mm (down to approximately 0.5 mm) in thickness can also be provided, although in practice such smaller samples are rarely needed.

Preferably, the tissue receiving space is open along one or both sides; thus the blades may be provided with respective opposing edges running generally perpendicular to the planes of the blades, thereby defining one, or two, longitudinal openings into the tissue receiving space. This is advantageous as it allows the device to cut much thinner sections than when side walls enclose the biopsy sample as with conventional cannula-type devices. The sampled tissue remains joined to the surrounding tissue at the openings whilst the device is initially inserted, and this supports the tissue, providing a better quality sample. It can be particularly useful to have the tissue held in place at the sides, during insertion of the device, when the sampled tissue is fibrous. After insertion the edges of the sample can be detached from the surrounding tissue by conventional surgical means or by mechanics of the biopsy device, as set out in more detail below.

Preferably the blades are substantially parallel to one another and planar. This assists in retaining large, flat tissue samples within the device and reduces trauma to the tissue to be sampled.

In a preferred embodiment both blades of the device are inserted simultaneously. It has been found that it is possible to produce blades of the required sharpness and rigidity necessary to allow the blades simply to be pushed manually into the tissue to be sampled by, for example, manufacturing these from stainless steel. However, where the tissue is particularly difficult to cut the blades can be made movable so that they can be inserted sequentially, one after the other, or so that they can be vibrated or oscillated with respect to one another, (alternatively, both blades may be oscillated in tandem). In one such variation of the device the blades pivot relative to one another in a small motion scissor action. Preferably, the blades are driven at a high vibrational frequency by a motor or vibrator. Advantageously the blades are driven at an ultrasonic frequency using, for example, an electrical oscillator and an ultrasonic transducer.

Preferably the blades taper towards the tip of the device, to assist in their insertion into the sampled tissue. Such a taper also assists in cutting the end of the tissue sample from the surrounding tissue as described below. In a preferred embodiment, the blades taper to a point.

The biopsy device advantageously also includes cutting means to cut the biopsy sample from the tissue after the device has been inserted. This allows for a staged cutting of the sample from the surrounding tissue, in which first upper and lower surfaces of the sample are cut and then residual points of attachment to the surrounding tissue are severed. This assists in maintaining the conformation of the biopsy sample, thereby providing a larger, usable sample. It also assists in obtaining a useful sample at each attempt, with consequent savings in cost and time and patient discomfort.

Preferably the cutting means cuts along the sides of the tissue receiving space. In one embodiment it cuts generally perpendicular to the planes of the blades; preferably it also cuts the end of the sample from the tissue adjacent the tip of the device. In a preferred arrangement this is achieved by slidably mounting a sample detachment blade on the device to cut the tissue on either side of the oppositely disposed blades of the tissue sampler. To cut the end of the sample, a portion of the detachment blade is preferably flexible and sprung inwardly to curve around the tip of the biopsy device as the detachment blade is advanced. This can be achieved by providing a carriage to which is attached at either side a blade guide with a sprung cutting extension which is biased to bend in towards the tip of the two oppositely disposed blades. The required resilient bias for the cutting portions of the detachment blade may be achieved, in this embodiment, by making the cutting extensions from sprung nickel titanium alloy. With this arrangement, the sample detachment blade's sprung extensions curve around the tip of the biopsy device after the side and end portions of the sample have been cut and help to protect and retain the sample as the biopsy device is withdrawn.

In alternative embodiments, separate sample detachment blades are advanced along either side of the two primary oppositely disposed blades. Additionally or alternatively, a cutting blade can be inserted over the top of the primary blades to cut the sample tip; this blade may be provided with cutting extensions at each side to cut along the side edges of the primary blades.

The detachment blade is preferably coupled to an actuation means so that it can be controlled to cut the sample from the tissue. In one embodiment the actuation means is linked to a button on the device running in a guide slot so that the sample detachment blade can be advanced after the biopsy device has been inserted. The actuation means may be resiliently biased to urge the carriage away from the tip of the biopsy device.

Preferably the device is suitable for one hand operation and may, for example, have a pistol grip and a trigger to operate the sample detachment blade.

In particularly preferred embodiments, a lymph node biopsy device has twin blades which lie in opposition in parallel planes, said blades having sharpened pointed tips to assist tissue penetration; and a detachment blade with inwardly curving flexible sharpened distal tips, which can by means of a track, move slidably along the twin blades so that in the retracted position the twin blades alone are exposed to the tissue to be sampled and can be offered to the tissue to cut the upper and lower surfaces of the biopsy. By advancing the detachment blade, the side walls and distal ends of the biopsy can then be cut. The said twin blades and detachment blade can be secured to either a) a handle sized to fit conveniently into the surgeon's hand, to which the twin blades are fixed; the detachment blade then being fixed to a button such that forward and backward movement of the button along the track results in forward and backward movement of the detachment blade along the twin blades; or b) a gun-like apparatus with a handle, trigger, pushrod and barrel such that the twin blades are fixed to the end of the barrel. In this arrangement the detachment blade, when in the retracted position, preferably lies within the barrel. Advancing the pushrod along the track within the barrel (achieved by means of applying pressure to the trigger) slides the detachment blade forward out of the barrel along the sides of the twin blades. Thus while the biopsy sample is held in position, gently compressed and sandwiched between the twin blades, the detachment blade tips cut the side walls and distal end of the biopsy sample. At the fully advanced position, the detachment blade tips overlay the distal ends of the twin blades. Within the body of the gun are arranged a lever, pivot and spring, or other similar arrangement, to provide a mechanical or electromechanical means by which pressure on the trigger results in forward movement of the detachment blade and extension of the spring, and relaxation of pressure on the trigger results in relaxation of the spring and withdrawal of the detachment blade.

These and other aspects of the invention will now be further described, by way of example only, with reference to the accompanying figures in which.

Referring first to FIGS. 1A to 1F, these show a blades 1 of a pair of oppositely disposed primary blades of a tissue sampler. These primary blades define top and bottom sides of a tissue sample receiving volume or space. The end of each of the primary blades has a sharpened edge 2 which tapers to a point. The angle included by the point at the tip may be selected according to tissue to be biopsied; it is typically between 30° and 60°, and preferably about 45°. The edge 2 should be sharp enough to easily penetrate soft tissue to be biopsied. The oppositely disposed primary blades 1 are attached to a handle (not shown in FIG. 1); they can, if desired, be arranged to be exchangeable to allow different blade sets to be used for different tissues and/or to facilitate sterilization or disposal after use.

Figure 1A:
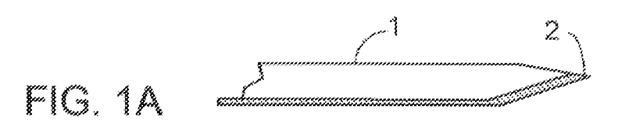
FIGS. 1A to 1L show, respectively, a perspective view of a blade of a tissue sampler from above and below (A and B); perspective, top, bottom and side views of twin blades of a tissue sampler of a biopsy device (C to F); a perspective view from below of a sample detachment blade (G); perspective views of a tissue sampler assembly comprising a pair of primary blades and a sample detachment blade in a retracted (H) and advanced (I) position; and side, top and bottom views of a sample detachment blade (J to L)
Figure 1B:
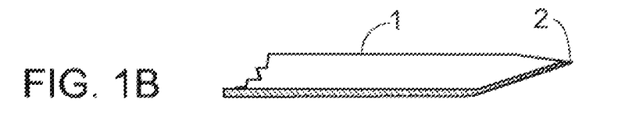
Figure 1C:
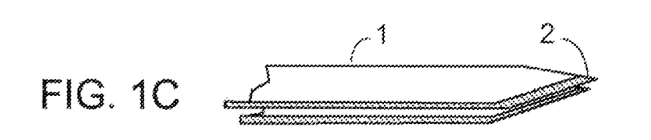
Figure 1D:
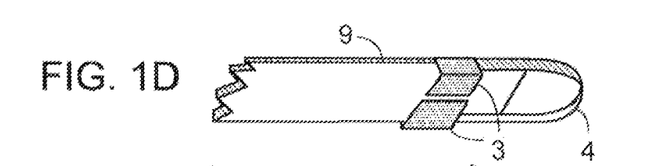
Figure 1E:
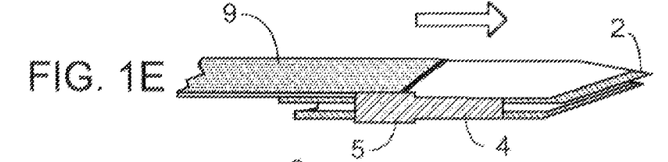
Figure 1F:
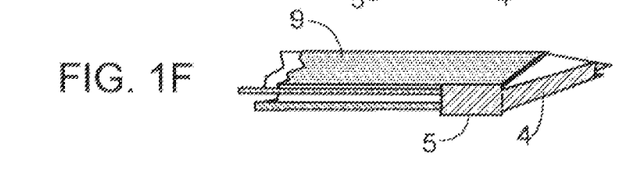
Figure 1G:
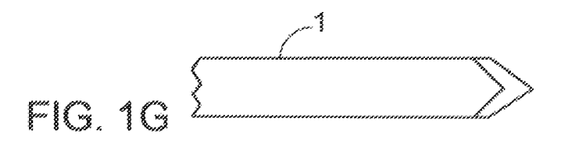
Figure 1H:
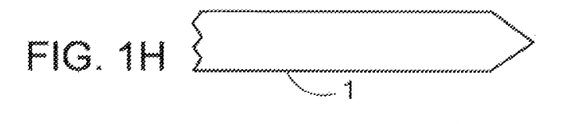
Figure 1I:
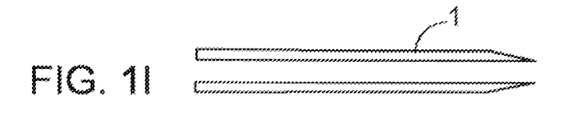
Figures 1J, 1K:
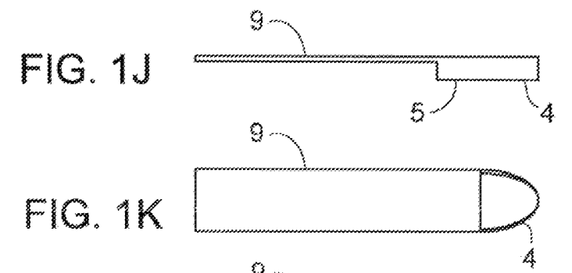
Figure 1L:
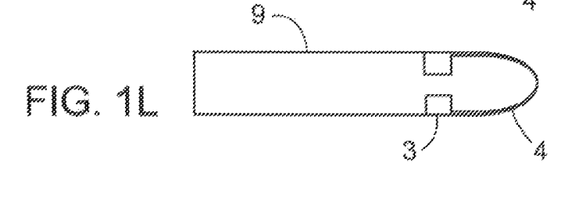

FIGS. 1G to 1L show versions of a sample detachment blade 9. As shown in FIGS. 1H and 1I, detachment blade 9 fits over primary blades 1 and mounts side cutting blade or blade guide portions 5 which clip around the underside of the primary blades by means of tabs 3. Blade portions 5 each have flexible cutting extensions 4 which abut against the side edges of the primary blades. Extensions 4 are arranged to be urged inwardly towards the sample receiving volume between primary blades 1, for example by arranging extensions 4 so that they naturally spring inwards. In this way, when the sample detachment blade is retracted as shown in FIG. 1H, the forward edges of extensions 4 abut the side edges of the primary blades, and cut along these edges as the detachment blade is advanced. When the ends of the extensions 4 reach the inward taper of the biopsy device tip, because they are sprung inwards, as the detachment blade is further advanced extensions 4 curve inwards to generally follow the contour of the biopsy device tip. They thus serve to sever the end of the biopsy sample from the surrounding tissue, as shown in FIG. 1I.

Figure 2:
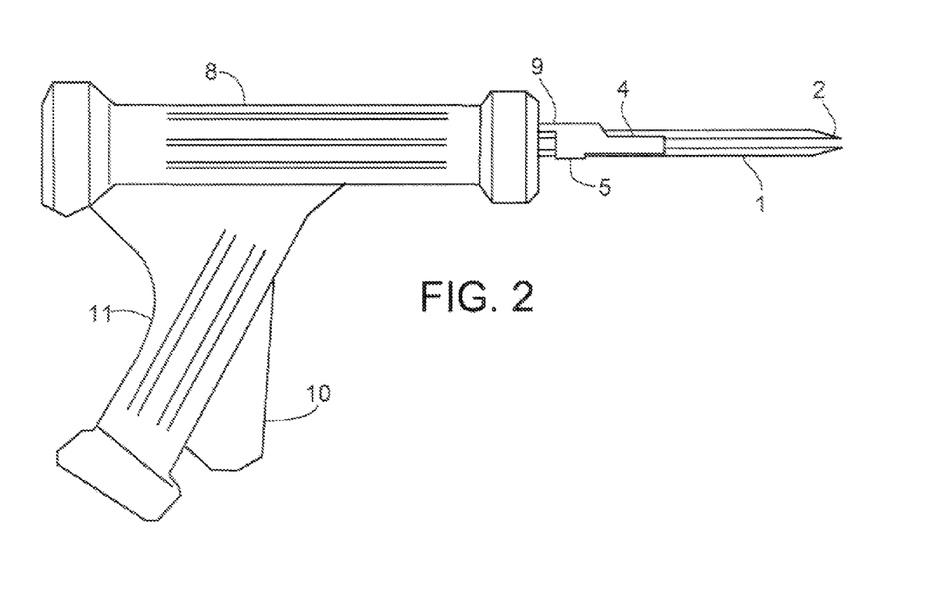
FIG. 2 shows a side view of a biopsy gun.

Referring now to FIG. 2, this shows components of FIG. 1 assembled into a biopsy gun. The gun comprises a barrel 8, a handle 11 and a trigger 10. Application of manual pressure on trigger 10 advances detachment blade 9 towards the sampling tip of the biopsy device.

Figure 3A:
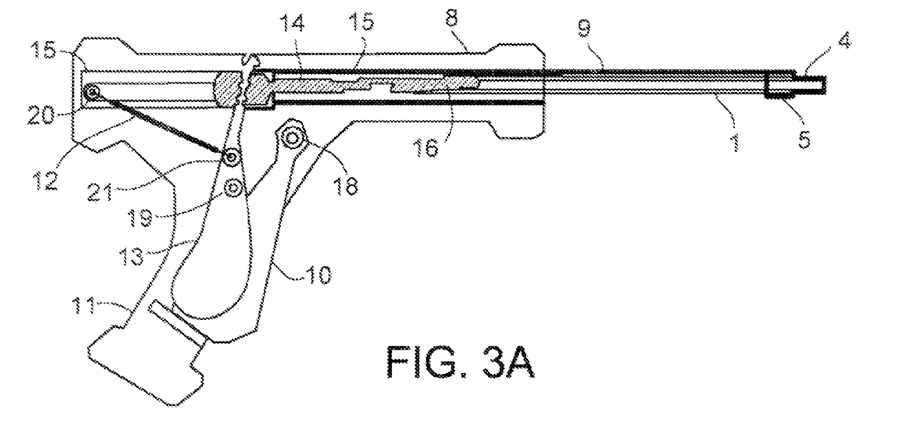
FIGS. 3A and 3B show, respectively, cross sections through the biopsy gun of FIG. 2 with a sample detachment blade in an advanced (A) and retracted (B) position.
Figure 3B:
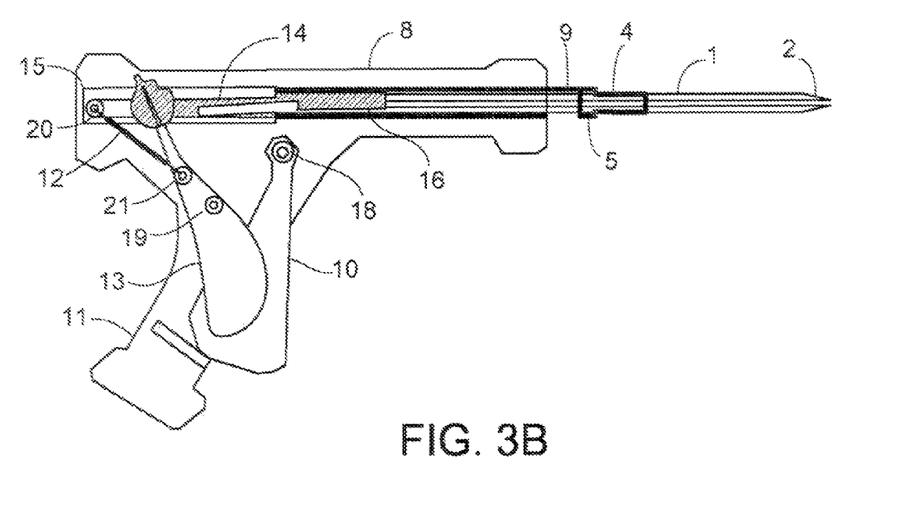
Figure 4A:
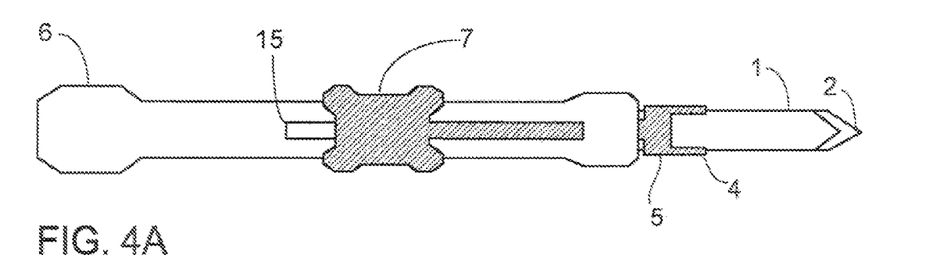
FIGS. 4A to D show, respectively, top (A and C) and side (B and D) views of a biopsy device with a sample detachment blade in a retracted (A and B) and advanced (C and D) position.
Figure 4B:
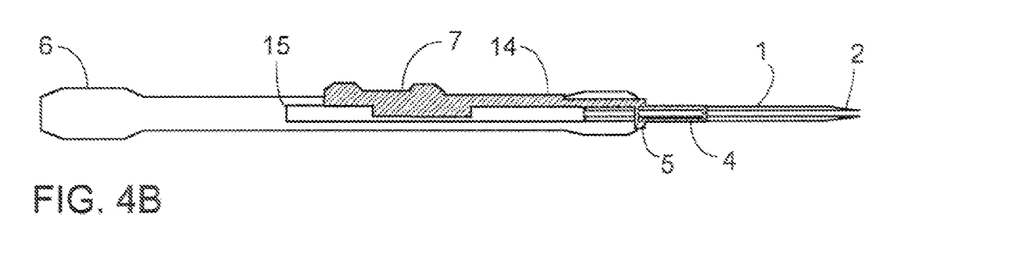
Figure 4C:
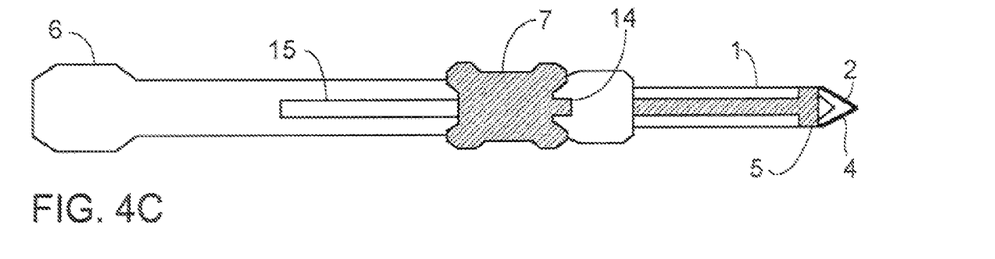
Figure 4D:
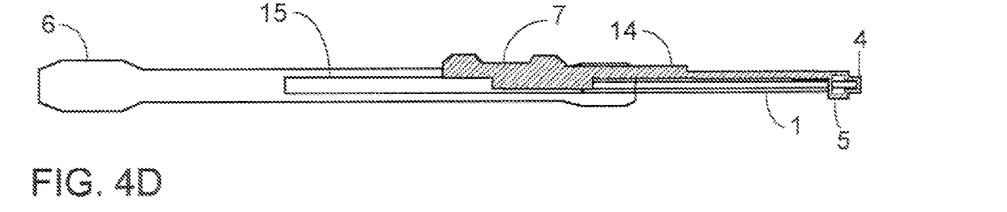

FIGS. 3A and 3B illustrate a mechanical means by which the application of pressure on the trigger results in the forward movement of the detachment blade 9. The twin blades 1 are fixed to the distal end (i.e. the end closest to the sampling tip) of the barrel 8 and the detachment blade 9 is free to move slidably along the track 15. The detachment blade proximal end (i.e. the end nearest the handle) is fixed to a pushrod 14 which has at its distal end 16 a stud which fixes it to the detachment blade 9. The pushrod 14 is also enclosed in the track 15 and its proximal end is attached to a lever 13, which rotates about a fixed pivot point 19. Application of pressure on the trigger effects rotation of the lever about point 19 which results in forward movement of the pushrod 14 and the detachment blade 9. A spring 12 is fixed to lever 13 at a point 21 at one end and to the proximal end of the barrel at a point 20 at the other end. The spring 12 is extended on application of pressure on the trigger 10, and ensures that the trigger 12 and pushrod 14 and detachment blade 9 return to the retracted position on relaxation of pressure on the trigger 10.

FIGS. 4A-D show an alternative embodiment of the device. This has the same arrangement of twin blades, fixed to handle 6, but detachment blade 9 is attached to a pushrod 14 and button 7 and slidably mounted in an internal track 15 of the handle. Thus sliding the button 7 forward and backwards along the track 15 effects forward and rearward movement of the pushrod 14 and detachment blade 9 relative to the twin primary blades 1.

The movable blades of the embodiment described with reference to FIG. 6 may employ a similar mechanism to those described above.

FIGS. 5A-D show a schematic representation of a procedure for biopsy of a soft tissue sample using the device (the handle of the device is not shown in these diagrams). The soft tissue is represented by skin 22 and subcutaneous tissue 23; this latter is the target tissue to be sampled in the illustration.

Figure 5A:
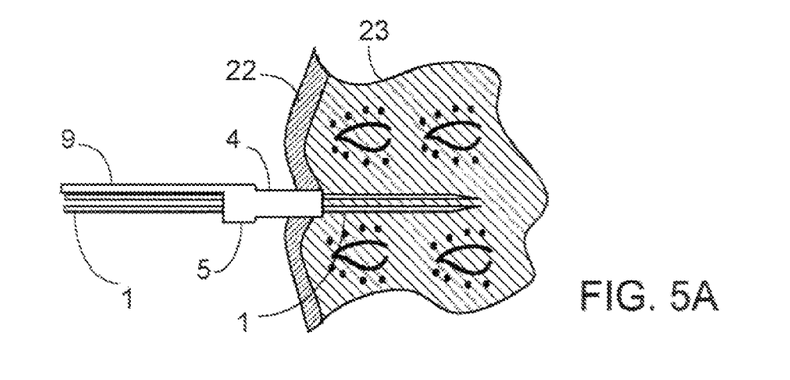
FIG. 5 shows steps in the use of a biopsy device to extract a tissue sample.

In FIG. 5A, a biopsy gun (not shown) is set in its retracted position—there is no pressure on the trigger 10, the twin blades are exposed, and the detachment blade is withdrawn from the device tip. In this position, the flexible inwardly curving sharpened tips 4 of the detachment blade 9 are held apart from their resting position by side walls of the twin blade 1. Local anaesthetic is applied and an incision is made in the skin so that there is direct access to the target tissue.

The operator holds the target tissue in place with the fingers of one hand and, with the other hand, holds the biopsy gun with the exposed twin blades 1 applied to the target tissue. With a single gentle stabbing motion, the device is advanced to the depth required (FIG. 5A). At this point, the upper and lower surfaces of the biopsy are cut, and the specimen, now sandwiched between the twin blades, is held gently in place by its attachment to the surrounding tissue at the sides and distal end.

Figure 5B:
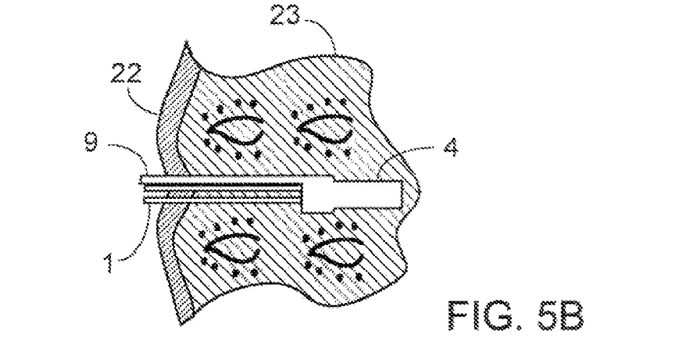

Pressure is then applied to the trigger, advancing the detachment blade 9 and in so doing cutting the side walls and distal end of the specimen (FIG. 5B). The inwardly curving flexible sharpened tips 4 of the detachment blade 9, as they are advanced, curve around the distal ends of the twin blade tips 2.

Figure 5C:
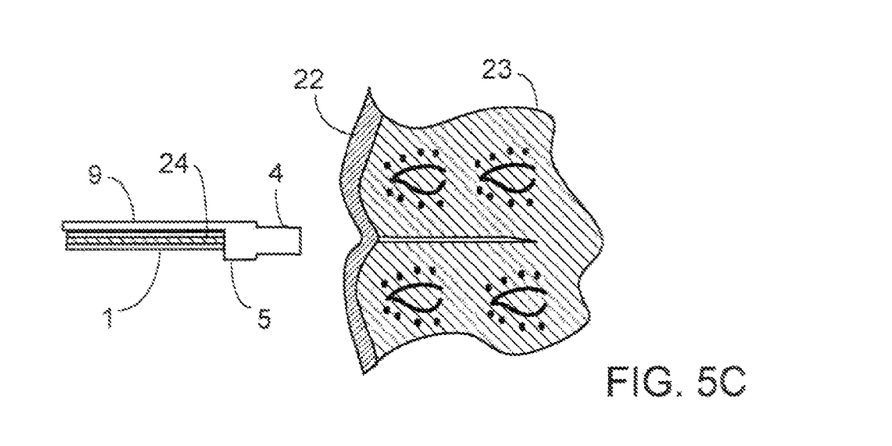

FIG. 5C shows retrieval of the intact specimen by withdrawal of the complete biopsy device, with the sample 24 protected by detachment blade 9 in its advanced position.

Figure 5D:
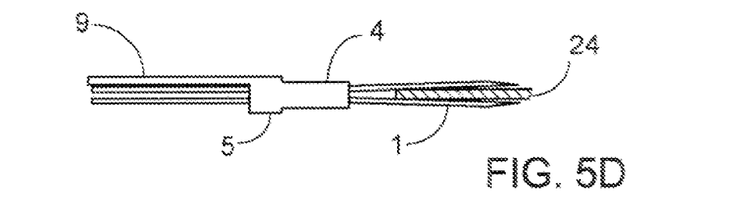
Figure 6A:
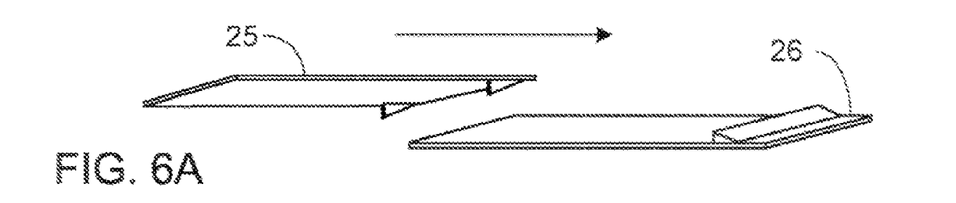
FIGS. 6a to f show, respectively, a perspective of a top blade and bottom blade of a biopsy device from the front, a perspective of the top blade and bottom blade from behind, bottom and top elevations of the top blade, and bottom and top elevations of the bottom blade.
Figure 6B:
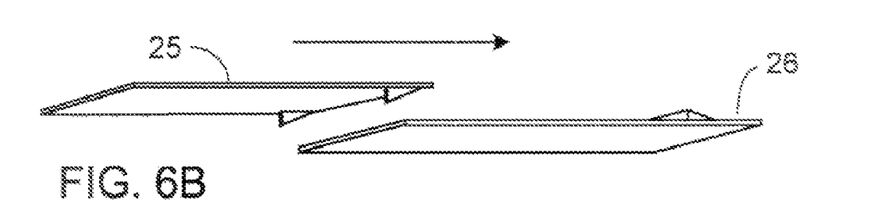
Figure 6C:
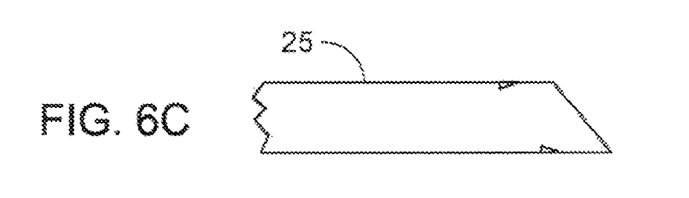
Figure 6D:
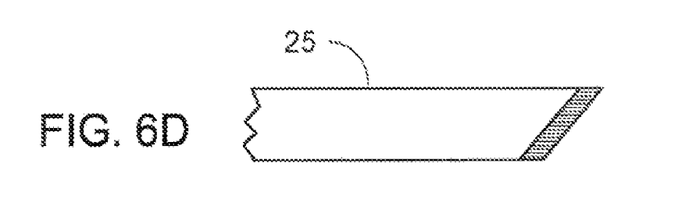
Figure 6E:
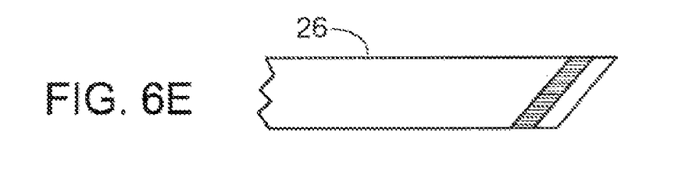
Figure 6F:
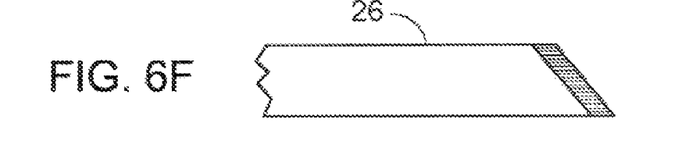
Figure 7A:
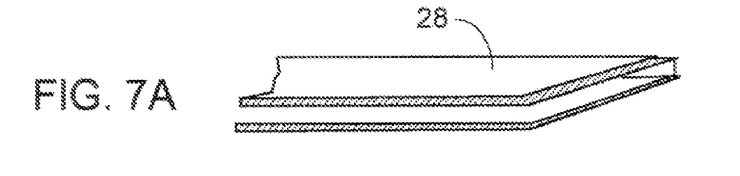
FIGS. 7a to g show, respectively, a perspective of a primary blade of a biopsy device from the front, a perspective of the primary blade from behind, a perspective of a detachment blade of a biopsy device from the front, a perspective of the primary blade and the detachment blade from the front, a top elevation of the primary blade, a bottom elevation of the primary blade, and a side elevation of the primary blade.
Figure 7B:
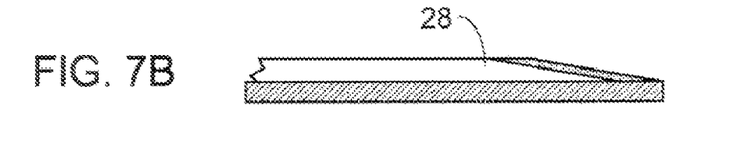
Figure 7C:
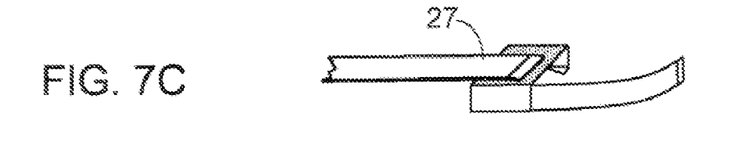
Figure 7D:
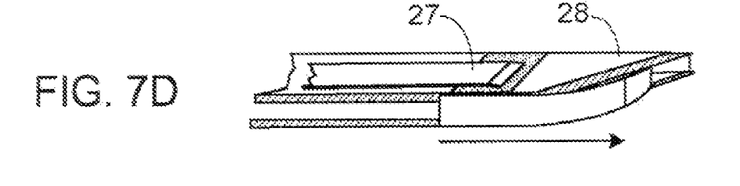
Figure 7E:
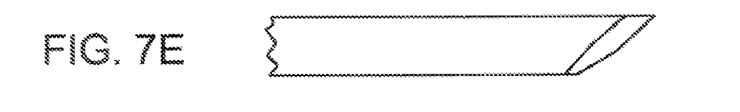
Figure 7F:
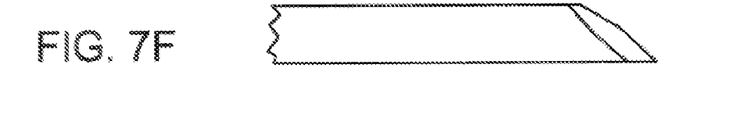
Figure 7G:
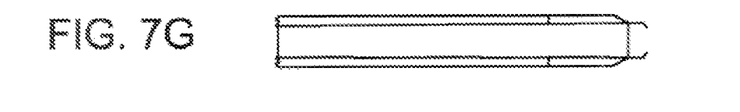

FIG. 5D shows withdrawal of the detachment blade to its retracted position, and sample dislodgement, which is achieved, for example, by gently tilting apart the twin blades 1.

Referring to FIG. 6, this shows a two blade design where a lower blade 26 is first advanced into tissue of interest, and then second, upper blade 25 is advanced to meet tip of bottom blade. The bottom blade has near its tip a sharpened elevation, such as an inwardly directed barb or edge, to assist in cutting and retention of the sample at the distal tip of the device when the two blades are both fully inserted. The upper blade 25 has near its tip and to the sides sharpened elevations, which cut the side walls of the biopsy as the top blade is advanced.

FIG. 7 shows a two blade design having a primary blade 28 which is three sided and which cuts the upper and lower surface and one side wall of tissue as it is advanced. Then, as a secondary detachment blade 27 is advanced along the primary blade, the remaining side wall and distal end of the biopsy is cut.

The above described biopsy devices provide many improvements on the existing biopsy devices: the double blade design is simple and economical to manufacture; it results in high quality specimens with little waste as the shape of the sample more closely conforms with the shape desired by the histopathologist; it effectively snares the biopsy specimen because of the staged cutting of the upper and lower surfaces of the biopsy by the twin blades, followed by the cutting of one or both side walls and then the distal end of the biopsy by the detachment blade; and it is safer for the patient because there is less risk of bleeding and it may obviate the need for a general anaesthetic or larger operative procedure. The procedure using this invention is less painful for the patient because there is less likelihood of failure, and the more efficient double blade design allows for the procurement of broader samples. The procedure is also less arduous for the operator because of the increased likelihood of retrieving the sample on the first attempt, and because less effort is needed to free the sample from the main body of the tissue.

No doubt many effective variations in this device will occur to the skilled person and the invention is not limited to the described embodiments. For example, the shapes of the blades' distal ends, and the handle style may be varied according to the intended use. Apart from lymph node biopsy, the present invention and aspects thereof can equally be applied to the biopsy of other soft tissues, particularly when the tissue of interest is readily accessible. Such situations especially arise in biopsies performed during open surgical operations, when skin, breast, muscle, liver, kidney, lung and other soft tissues may require biopsy. The device also has applications where biopsies are taken during post mortem examination. The procedure and device can also be used in animal practice, for both vivo and post mortem applications.

The invention claimed is:

1. A biopsy device comprising a tissue sampler, the tissue sampler having a generally longitudinal shape with a longitudinal axis defined by a direction of insertion of the tissue sampler into tissue to be sampled, the tissue sampler comprising a pair of first and second blades the blades each having a substantially planar surface, said two planar surfaces being oppositely disposed and parallel to one another and spaced apart from one another in a direction perpendicular to said planar surfaces, the blades having front, spaced edges to cut the sampled tissue as the device is inserted into the tissue, one blade being independently actuatable with respect to the other along said longitudinal axis, the two blades and the space between the blades defining a tissue receiving space to receive tissue to be sampled, said tissue receiving space having two oppositely disposed substantially planar, parallel sides defined by said blades, the tissue sampler further comprising a cutter to cut the sample from the tissue after the device has been inserted.

2. A biopsy device as claimed in claim 1 wherein the cutter comprises a third blade.

3. A biopsy device as claimed in claim 2 wherein the third blade is disposed outside the tissue receiving space.

4. A biopsy device as claimed in claim 1, 2 or 3 wherein the tissue receiving space is open along a third side, said third side having edges defined by opposing edges of the oppositely disposed blades.

5. A biopsy device as claimed in claim 4, wherein the tissue receiving space is open along a fourth side, opposite the third side, said forth side having edges defined by opposing edges of the oppositely disposed blades.

6. A biopsy device as claimed in claim 4 or 5, wherein the cutter is configured to cut the tissue adjacent at least one side edge of the blades.

7. A biopsy device as claimed in claim 1, further comprising drive means to oscillate one of the pair of blades relative to the other.

8. A biopsy device as claimed in claim 1, further comprising at least one side cuffing blade, wherein said side cuffing blade cuts a side of the sampled tissue said side being defined by opposing edges of said oppositely disposed blades, wherein the side cutting blade is attached to one of said oppositely disposed blades.

9. A biopsy device as claimed in claim 1, wherein one of said oppositely disposed blades is configured to define a front interior wall of said tissue receiving space near the tip of the device and extending generally perpendicular to said longitudinal axis.

10. A biopsy device as claimed in claim 1, wherein the width of at least one of the oppositely disposed blades in a plane defined by the blade tapers towards the tip of the device.

11. A biopsy device as claimed in claim 10, wherein the cutter comprises a blade to cut along at least one open side of the tissue receiving space.

12. A biopsy device as claimed in claim 11, wherein the cutter is configured to cut across an end of the sample adjacent the tip of the device.

13. A biopsy device as claimed in claims 11 or 12, wherein the cutter is configured to cut along both sides of the tissue receiving space.

14. A biopsy device as claimed in claim 1, wherein the cutter comprises a movable sample detachment blade slidably mounted on the tissue sampler for cutting the sampled tissue along a side or sides of the tissue receiving space defined by the oppositely disposed blades.

15. A biopsy device as claimed in claim 14, wherein a portion of the movable sample detachment blade is flexible and biased inwardly towards the tissue receiving space to assist in severing the end of the tissue sample adjacent the device tip.

16. A biopsy device as claimed in claim 14 or 15, wherein the movable sample detachment blade comprises a pair of oppositely disposed blade portions.

17. A biopsy device as claimed in claim 14 further comprising an actuation system to move the movable blade for assisted sample detachment.

18. A biopsy device as claimed in claim 17, configured for one-hand operation.

19. A biopsy device as claimed in claim 17, further comprising a handle attached to the tissue sampler, and wherein the actuation system comprises a spring operated by a trigger.

20. A biopsy device as claimed in claim 1, wherein the tissue receiving space is closed on a third side and provided with a movable blade to cut along a fourth side of the space.

21. A biopsy device as claimed in claim 20, wherein the oppositely disposed blades taper towards the third side and wherein the movable blade is biased towards the third side to facilitate cutting across the end of a tissue sample.

22. A soft tissue biopsy device comprising a tissue sampler, the tissue sampler having a generally longitudinal shape with a longitudinal axis defined by a direction of insertion of the tissue sampler into soft tissue to be sampled, the tissue sampler comprising a pair of oppositely disposed blades each having a substantially planar surface, said two planar surfaces being oppositely disposed and parallel to one another and spaced apart from one another in a direction perpendicular to said planar surfaces, wherein the pair of blades comprises first and second blades, one blade being independently actuatable with respect to the other along said longitudinal axis, the blades defining two sides of a tissue receiving space to receive soft tissue to be sampled and, said blades, having front edges to cut the sampled soft tissue.

23. A biopsy device as claimed in claim 22, wherein the tissue receiving space is open along a third side, said third side having edges defined by edges of the oppositely disposed blades.

24. A biopsy device as claimed in claim 23, wherein the tissue receiving space is open along a fourth side, opposite the third side, said fourth side having edges defined by edges of the oppositely disposed blades.

25. A biopsy device as claimed in claim 23 further comprising a cutter to cut the sample from the tissue after the device has been inserted.

26. A biopsy device as claimed in claim 25 wherein the cutter is configured to cut along at least one open side of the tissue receiving space.

27. A biopsy device as claimed in any one of claims 22 to 24, wherein the first and second blades are configured to be advanced sequentially into the sampled tissue.

28. A biopsy device as claimed in claim 27, further comprising drive means to oscillate one blade relative to the other.

29. A biopsy device as claimed in any one of claims 22 to 24 further comprising at least one side cutting blade, wherein said side cutting blade cuts a side of the sample tissue defined by opposing edges of said oppositely disposed blades, wherein side cutting blade is attached to one of said oppositely disposed blades.

30. A biopsy device as claimed in any one of claims 22 to 24 wherein one of said oppositely disposed blades has a raised portion towards the tip to define a front interior wall of said tissue receiving space extending generally perpendicular to said longitudinal axis to assist in retaining a tissue sample.

* * * * *

UNITED STATES PATENT AND TRADEMARK OFFICE
CERTIFICATE OF CORRECTION

| | | |
|---|---|---|
| PATENT NO. | : 7,722,548 B2 | Page 1 of 1 |
| APPLICATION NO. | : 10/258323 | |
| DATED | : May 25, 2010 | |
| INVENTOR(S) | : Paul Laurence Cervi | |

It is certified that error appears in the above-identified patent and that said Letters Patent is hereby corrected as shown below:

Title Page (item 57) Column 2, Line 13, delete "twixt" and insert -- twin --, therefor.

Column 8, Line 57, Claim 5, delete "forth" and insert -- fourth --, therefor.

Column 8, Line 66, Claim 8, delete "cuffing blade," and insert -- cutting blade, --, therefor.

Column 10, Line 38, Claim 29, delete "cuffing" and insert -- cutting --, therefor.

Signed and Sealed this

Twenty-first Day of December, 2010

David J. Kappos
*Director of the United States Patent and Trademark Office*